(12) United States Patent
Raines et al.

(10) Patent No.: US 11,420,042 B2
(45) Date of Patent: Aug. 23, 2022

(54) SYSTEMS AND METHODS FOR DELIVERING NEUROSTIMULATION USING EXOGENOUS ELECTRODES

(71) Applicant: Advanced Neuromodulation Systems, Inc., Plano, TX (US)

(72) Inventors: Aaron Raines, Dallas, TX (US); Manasi Reardon, Allen, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 0 days.

(21) Appl. No.: 17/119,204

(22) Filed: Dec. 11, 2020

(65) Prior Publication Data

US 2022/0184380 A1 Jun. 16, 2022

(51) Int. Cl.
*A61N 1/36* (2006.01)
*A61N 1/04* (2006.01)

(52) U.S. Cl.
CPC ......... *A61N 1/0456* (2013.01); *A61N 1/0496* (2013.01); *A61N 1/36034* (2017.08)

(58) Field of Classification Search
CPC . A61N 1/0456; A61N 1/36034; A61N 1/0496
See application file for complete search history.

(56) References Cited

U.S. PATENT DOCUMENTS

| | | | |
|---|---|---|---|
| 8,388,541 B2 | 3/2013 | Messerly et al. | |
| 9,067,071 B2 | 6/2015 | Sanders et al. | |
| 9,456,766 B2 | 10/2016 | Cox et al. | |
| 9,554,716 B2 | 1/2017 | Burnside et al. | |
| 9,561,369 B2 | 2/2017 | Burnes et al. | |
| 10,299,693 B2 | 5/2019 | Sarkar et al. | |
| 10,524,691 B2 | 1/2020 | Newman et al. | |
| 10,524,832 B2 | 1/2020 | Masson | |
| 2009/0248122 A1* | 10/2009 | Pianca | A61N 1/0551 607/115 |
| 2016/0213509 A1* | 7/2016 | Petitt | A61F 7/02 |
| 2018/0001086 A1* | 1/2018 | Bartholomew | B29C 35/02 |
| 2019/0001129 A1* | 1/2019 | Rosenbluth | A61N 1/0476 |
| 2019/0167973 A1* | 6/2019 | Pisarev | A61N 1/36031 |
| 2021/0052884 A1* | 2/2021 | Jashek | A61N 1/0456 |
| 2021/0353173 A1 | 11/2021 | Newman et al. | |

* cited by examiner

*Primary Examiner* — Ankit D Tejani
*Assistant Examiner* — Joshua Brendon Solomon
(74) *Attorney, Agent, or Firm* — Armstrong Teasdale LLP

(57) ABSTRACT

The present disclosure provides systems and methods for exogenous neurostimulation. An exogenous neurostimulation system includes an electrode pad comprising a plurality of electrodes configured to be applied to skin of a patient, and a pulse generator communicatively coupled to the electrode pad, the pulse generator operable to generate burst waveforms for delivery to the skin of the patient via the electrode pad.

18 Claims, 5 Drawing Sheets

SYSTEMS AND METHODS FOR DELIVERING NEUROSTIMULATION USING EXOGENOUS ELECTRODES

A. FIELD OF THE DISCLOSURE

The present disclosure relates generally to neurostimulation systems, and more particularly to neurostimulation systems using exogenous electrodes.

B. BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors. Types of neurostimulation include, for example, deep brain stimulation (DBS), spinal cord stimulation (SCS), peripheral nerve stimulation, and Dorsal Root Ganglion (DRG) stimulation.

For patients with chronic pain, pain may persist for over six months or for longer than generally to be expected for recovery to a particular disease, injury, or surgery. Chronic pain is often the result of an illness or injury, and is the most common cause of disability in the United States, with over 25 million adults in the United States having experienced chronic pain lasting three months or more.

To manage pain more effectively, implantable neurostimulation systems (e.g., DBS, SCS, and DRG stimulation systems) may be implanted in a patient through an invasive procedure. Prior to patients being considered for an implantable neurostimulation system, several other pain management methods may have been attempted (e.g., medications such as gabapentin or pregabalin, interventional or injection-type pain management therapies such as epidurals or nerve blocks, surgical procedures such as discectomy or ablations, and/or other methods such as massage, acupuncture, physical therapy, etc.). However, if these pain management methods are ineffective or lead to systemic side effects, an implantable neurostimulation may be considered.

As noted above, however, implantable neurostimulation systems require an invasive procedure for implantation. Accordingly, it would be desirable to provide an exogenous neurostimulation system that achieves at least some of the benefits of an implantable neurostimulation without requiring an invasive implantation.

BRIEF SUMMARY OF THE DISCLOSURE

In one embodiment, the present disclosure is directed to an exogenous neurostimulation system. The system includes an electrode pad comprising a plurality of electrodes configured to be applied to skin of a patient, and a pulse generator communicatively coupled to the electrode pad, the pulse generator operable to generate burst waveforms for delivery to the skin of the patient via the electrode pad.

In another embodiment, the present disclosure is directed to a method of assembling an exogenous neurostimulation system. The method includes providing an electrode pad including a plurality of electrodes configured to be applied to skin of a patient, and communicatively coupling a pulse generator to the electrode pad, the pulse generator operable to generate burst waveforms for delivery to the skin of the patient via the electrode pad.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1A:
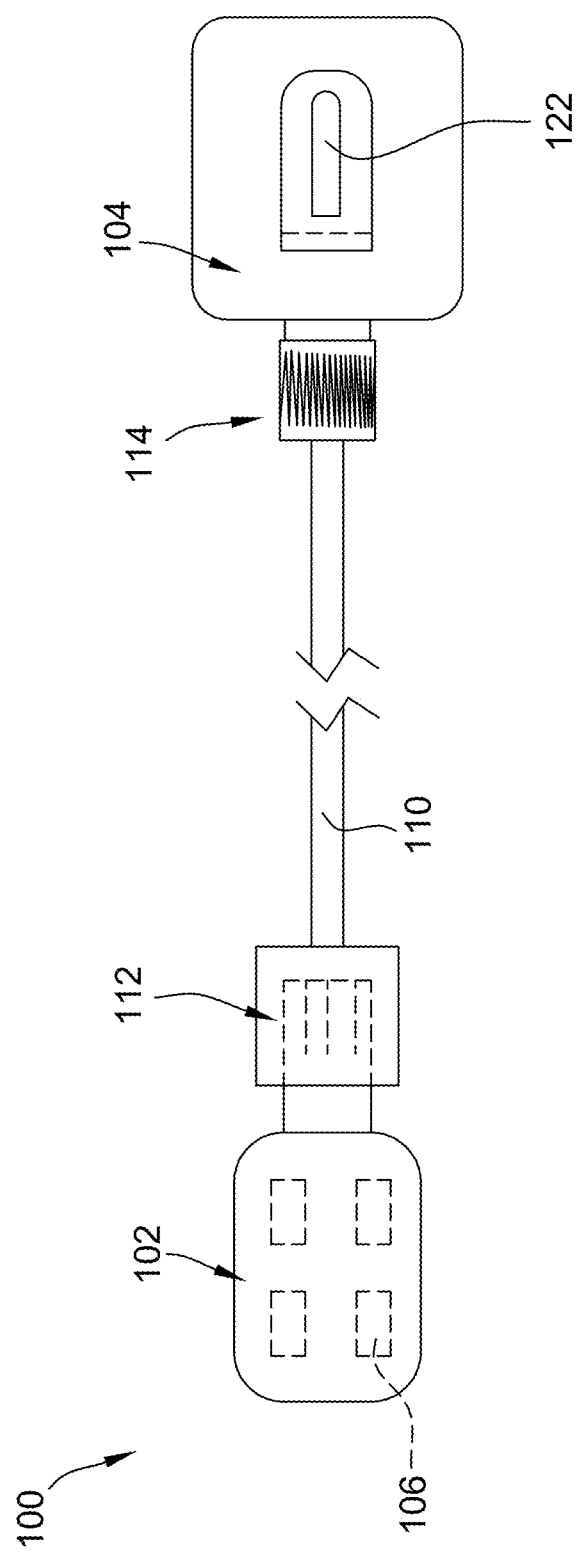
FIG. 1A is a plan schematic view of one embodiment of an exogenous neurostimulation system.

The present disclosure provides systems and methods for exogenous neurostimulation. An exogenous neurostimulation system includes an electrode pad comprising a plurality of electrodes configured to be applied to skin of a patient, and a pulse generator communicatively coupled to the electrode pad, the pulse generator operable to generate burst waveforms for delivery to the skin of the patient via the electrode pad.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS) and Complex Regional Pain Syndrome (CRPS).

Neurostimulation systems generally include a pulse generator and one or more leads. A stimulation lead includes a lead body of insulative material that encloses wire conductors. The distal end of the stimulation lead can include multiple electrodes that intimately impinge upon patient tissue and are electrically coupled to the wire conductors. The proximal end of the lead body can include multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

At least some known neurostimulation systems are implantable in a patient (e.g., using an invasive procedure). However, the systems and methods described herein are directed to exogenous neurostimulation systems (i.e., neurostimulation systems that are not implanted, but that instead include external electrodes applied to a patient's skin), as discussed in further detail herein.

In implantable neurostimulation systems, tonic and/or burst waveforms may be used to treat chronic pain. For example, applying burst waveforms (e.g., BurstDR®) to appropriate neural targets may result in superior pain therapy outcomes, significantly reduced power consumption, and reduced habituation (BurstDR is a registered trademark of St. Jude Medical, Inc. of St. Paul, Minn.). Further, flexible programmability of implantable neurostimulation systems facilitates realizing improved therapy and patient experiences.

The systems and methods described herein provide an exogenous (i.e., not implanted) neurostimulation system that is capable of providing stimulation waveforms similar to implanted neurostimulation systems (e.g., BurstDR). This facilitates achieving non-invasive therapy that may be used early in a treatment continuum.

At least some known transcutaneous electrical nerve stimulation (TENS) systems deliver electrical stimulation through skin electrodes to nerve targets. However, TENS systems typically are limited to delivering tonic pulses or variations of tonic pulses. Further, the amplitudes of pulses in a TENS systems are usually adjusted to relatively high amplitudes that result in a comfortable sensation for the patient while remaining below the patient's motor threshold. At least some known TENS systems may also result in habituation, and may be generally ineffective in treating chronic pain in the long term.

In contrast, the systems and methods described herein provide non-invasive stimulation using an exogenous neurostimulation system that delivers relatively complex waveforms (e.g., BurstDR) that are effective in treating pain without causing uncomfortable sensations to the skin or muscle of the patient. The exogenous neurostimulation system may deliver superior pain therapy as compared to at least some known TENS systems, and may also provide less unwanted sensation and less habituation. Further, while TENS systems typically stimulate muscles, the exogenous neurostimulation system described herein may be used to target superficial nerves. For example, the exogenous neurostimulation system described herein may be used to electrically stimulate peripheral nerve targets including, for example, a common peroneal nerve, a superficial peroneal nerve, a deep peroneal nerve, a lateral femoral cutaneous nerve, a tibial nerve, a saphenous nerve, a sciatic nerve, a femoral nerve, an Ilioinguinal nerve, an iliohypogastric nerve, a genitofemoral nerve, an intercostal nerve, a cluneal nerve, lateral branches of sacral nerves, dorsal cutaneous nerves of cervical, thoracic, and lumbar spines, median, ulnar, radial, axillary, suprascapular, supra- and infra-orbital nerves, temporo-auricular nerves, trigeminal divisions, post ganglionic nerves, or C2 fibers at the posterior occiput.

In at least some of the embodiments described herein, the exogenous neurostimulation system includes a disposable pad that can include an array of electrodes. This allows for implementing multiple different therapy programs and amplitudes using the electrode pad. In contrast, TENS systems typically include pads that each include only a single electrode, and only allow amplitude adjustment of applied stimulation.

Using the exogenous neurostimulation system described herein, patients and clinicians may select from a variety of pads to choose an electrode array that best meets their therapy needs (e.g., a pad with a few large electrodes, a pad with many small electrodes, pads with different array patterns, etc.). Further, using an array of electrodes, patients and clinicians can adjust a target therapy area as needed without having to reposition the pad, while minimizing paresthesia to surrounding areas.

Figure 1B:
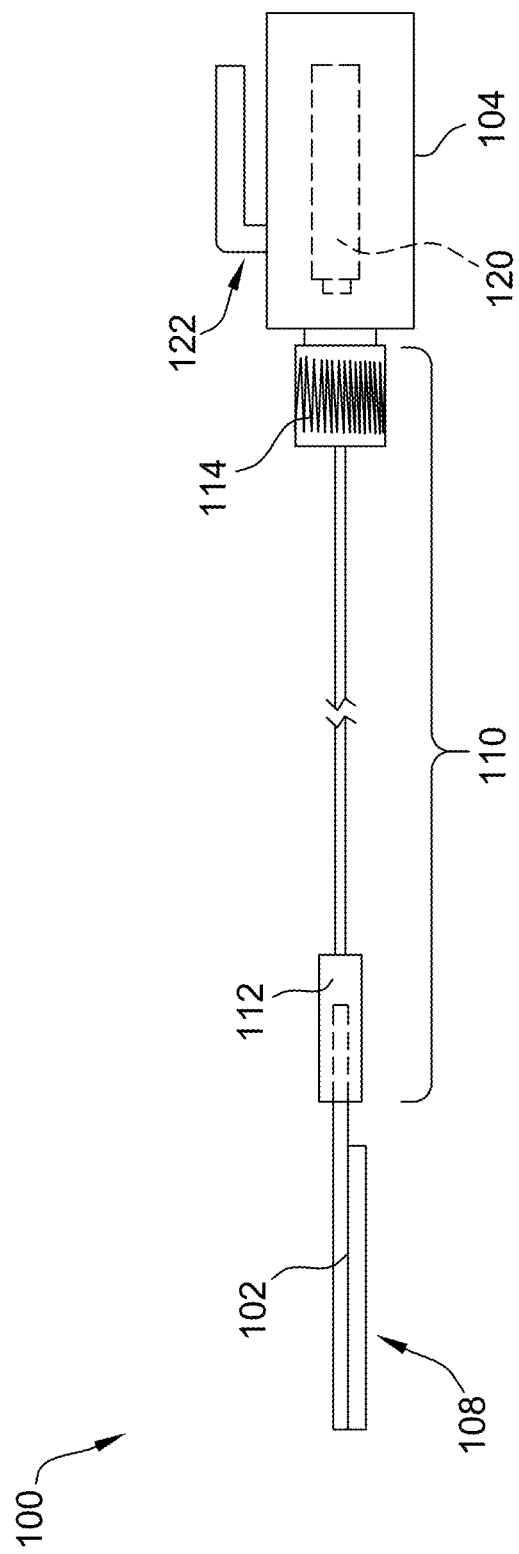
FIG. 1B is a side schematic view of the exogenous neurostimulation system shown in FIG. 1A.

Referring now to the drawings, FIG. 1A is a plan schematic view of one embodiment of an exogenous neurostimulation system 100. FIG. 1B is a side schematic view of exogenous neurostimulation system 100. System 100 includes an electrode pad 102 communicatively coupled to a pulse generator 104. In this embodiment, electrode pad 102 is in wired communication with pulse generator 104. Alternatively, electrode pad 102 may be in wireless communication with pulse generator 104. To alleviate chronic pain, electrode pad 102 may be adhered at any suitable location on the patient's body (e.g., on the patient's shoulder, knees, ankle, hip, groin, etc.)

Electrode pad 102 may be disposable after one or more uses, and includes a plurality of electrodes 106 arranged in an array. In this embodiment, electrode pad 102 includes four electrodes 106 arranged in a grid pattern. Alternatively, as will be appreciated by those of skill in the art, electrode pad 102 may include any suitable number of electrodes arranged in any suitable pattern. Electrode pad 102 includes an adhesive layer 108 for adhering electrode pad 102 to a patient. After one or more uses, adhesive layer 108 may degrade, and electrode pad 102 may be disposed of and replaced with a new electrode pad 102.

As shown in FIGS. 1A and 1B, a cable 110 extends between electrode pad 102 and pulse generator 104. Cable 110 includes a first connector 112 (e.g., a ribbon connector) for connecting to electrode pad 102, and a second connector 114 for connecting to pulse generator 106.

Pulse generator 104 may be powered, for example, by one or more batteries 120 (e.g., replaceable alkaline batteries). Further, in this embodiment, pulse generator 104 includes a clip 122 for attaching pulse generator 104 to a patient's clothing, belt, etc.

Pulse generator 104 is adapted to generate electrical pulses for application to the skin of a patient. An example processor and associated charge control circuitry for a pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 104. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Pulse generator 104 may be controlled using a controller device implemented within or communicatively coupled to pulse generator 104. For example, the controller device may be a mobile computing device (e.g., a mobile phone) communicatively coupled to pulse generator 104 using a near-field communication scheme (e.g., Bluetooth). Also, multiple controller devices may be provided for different types of users (e.g., the patient or a clinician). The controller device may be implemented by utilizing a suitable handheld processor-based system that possesses wireless communication capabilities. Software is typically stored in a memory of a controller device to control the various operations of the controller device. Further, the controller device may provide one or more user interfaces to allow the user to operate pulse generator 104 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc.

Pulse generator 104 modifies its internal parameters in response to the control signals from the controller device to vary the stimulation characteristics of stimulation pulses transmitted through electrode pad 102 to the skin of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 2:
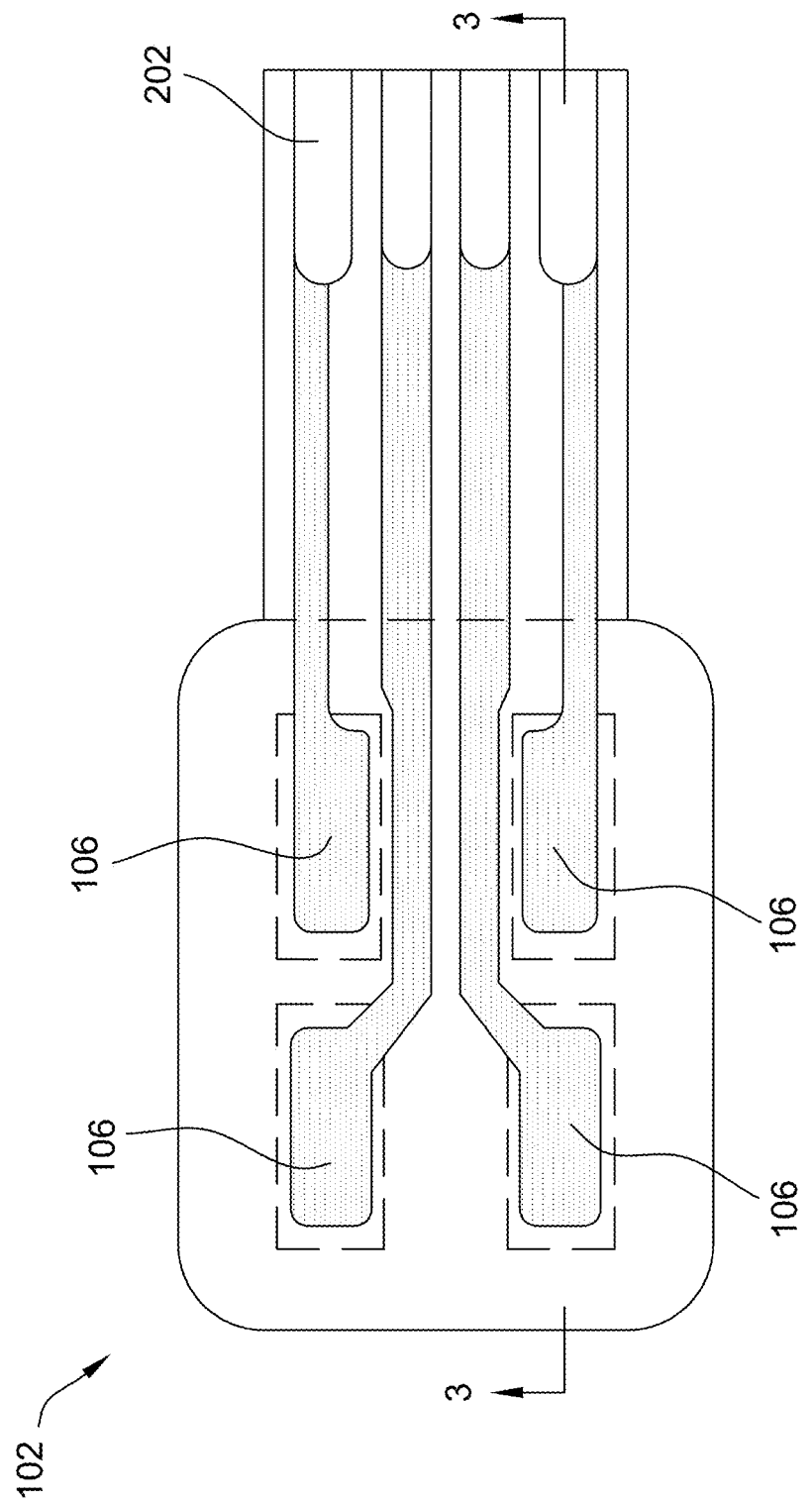
FIG. 2 is an enlarged plan view of an electrode pad that may be used with the exogenous neurostimulation system shown in FIG. 1A.
Figure 3:
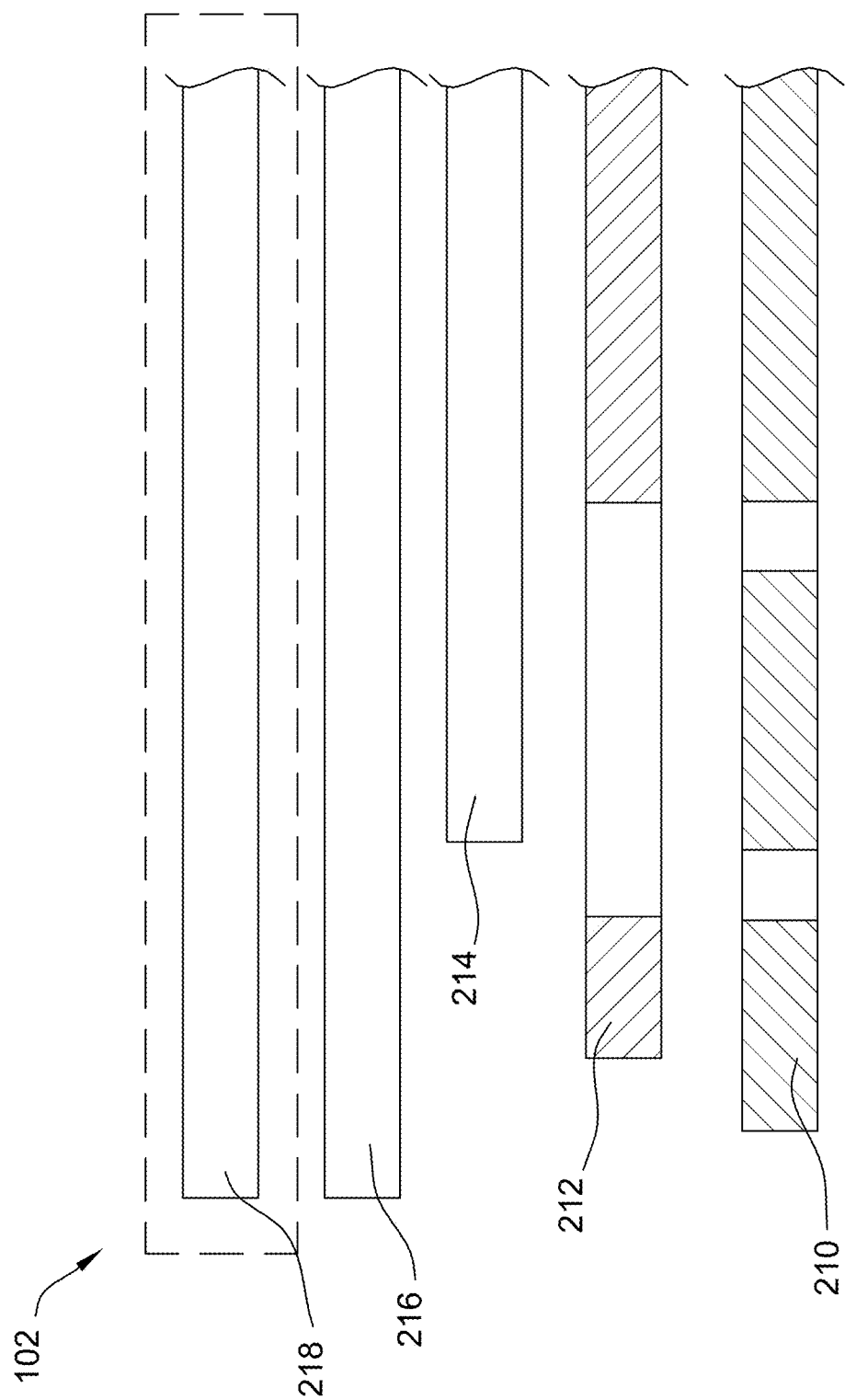
FIG. 3 is an exploded cross-section view of a portion of the electrode pad shown in FIG. 2 taken along line 3-3.

FIG. 2 is an enlarged plan view of electrode pad 102. FIG. 3 is a cross-sectional view of a portion of electrode pad 102 taken along line 3-3 (shown in FIG. 2). As shown in FIG. 2, each electrode 106 is electrically coupled to an associated contact 202 (e.g., a ribbon contact). Contacts 202 engage corresponding terminals in first connector 112. Alternatively, electrode pad 102 may connect to first connector 112 using any suitable mechanism, such as, for example, a relatively simple snap connector.

In this embodiment, to produce electrode pad 102 at a relatively low cost (in light of the fact that electrode pad may be disposable), electrode pad 102 is implemented using flexible circuit technology. Specifically, as shown in FIG. 3, electrode pad 102 includes a conductive adhesive layer 210, an insulation layer 212, a conductive layer 214, and a substrate layer 216.

Conductive adhesive layer 210 is configured to adhere to the skin of a patient. Insulation layer 212 covers wires extending from electrodes 106 and serves as a screen between conductive layer 214 and conductive adhesive layer 210. Conductive layer 214 defines electrodes 106, and conductive layer 214 is supported by substrate layer 216, as will be appreciated by those of skill in the art.

In some embodiments, electrode pad 102 further includes a non-conductive adhesive layer 218 attached to substrate layer 216. In embodiments where pulse generator 104 communicates wirelessly with electrode pad 102, pulse generator 104 may be adhered directly to electrode pad 102 using non-conductive adhesive layer 218, reducing an overall footprint of exogenous neurostimulation system 100. Alternatively, non-conductive adhesive layer 218 may be omitted in some embodiments. As noted above, although four electrodes 106 are shown in FIG. 2, those of skill in the art will appreciate that any suitable number and pattern of electrodes 106 may be used.

Figure 4B:
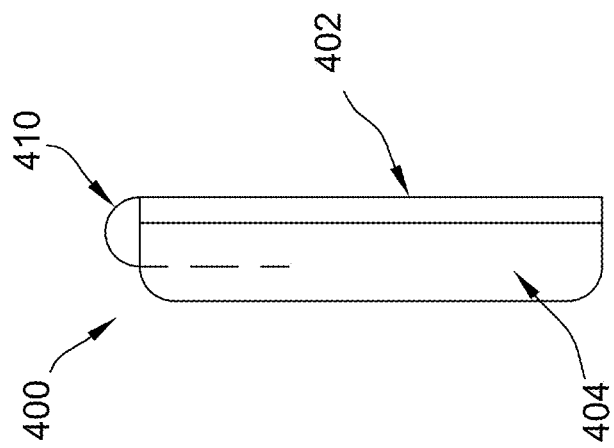
FIG. 4B is a side schematic view of the exogenous neurostimulation system shown in FIG. 4A.
Figure 4A:
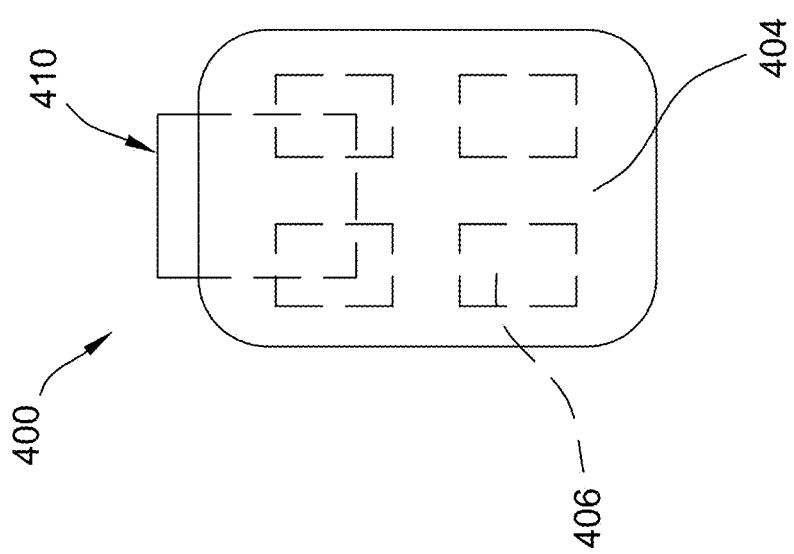
FIG. 4A is a plan schematic view of another embodiment of an exogenous neurostimulation system.

FIG. 4A is a plan schematic view of another embodiment of an exogenous neurostimulation system 400. FIG. 4B is a side schematic view of exogenous neurostimulation system 400. Similar to exogenous neurostimulation system 100, exogenous neurostimulation system 400 includes an electrode pad 402 having a plurality of electrodes 406, and a pulse generator 404. In this embodiment, however, pulse generator 404 is mechanically attached directly to electrode pad 402 (e.g., via a non-conductive adhesive layer, such as non-conductive adhesive layer 218 (shown in FIG. 3)). That is, in this embodiment, pulse generator 404 is small enough to be positioned on electrode pad 402. Pulse generator 404 may be powered, for example, using rechargeable battery cells (e.g., lithium ion battery cells).

Operation of pulse generator 404 may be controlled, for example, by a separate programmer device (e.g., a mobile computing device) communicatively coupled to pulse generator 404. As discussed above, pulse generator 404 and electrode pad 402 may be in wired or wireless communication with one another. For example, in FIGS. 4A and 4B, pulse generator 404 and electrode pad 402 are communicatively coupled to one another via a ribbon tab 410. Alternatively, pulse generator 404 and electrode pad 402 may communicate wirelessly. When electrode pad 402 degrades after one or more uses, electrode pad 402 may be detached from pulse generator 404 and discarded, and a new electrode pad 402 may be attached to pulse generator 404.

The embodiments described herein are directed to exogenous neurostimulation. An exogenous neurostimulation system includes an electrode pad comprising a plurality of electrodes configured to be applied to skin of a patient, and a pulse generator communicatively coupled to the electrode pad, the pulse generator operable to generate burst waveforms for delivery to the skin of the patient via the electrode pad.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An exogenous neurostimulation system comprising:
   an electrode pad comprising a plurality of electrodes configured to be applied to skin of a patient, the electrode pad further comprising:
      a conductive adhesive layer configured to adhere to the skin of the patient;
      an insulation layer adjacent the conductive adhesive layer;
      a conductive layer adjacent the insulation layer and defining the plurality of electrodes, the insulation layer positioned between the conductive layer and the conductive adhesive layer;
      a substrate layer adjacent the conductive layer and supporting the conductive layer, the conductive layer positioned between the substrate layer and the insulation layer; and
      a plurality of contacts corresponding to the plurality of electrodes, each contact electrically coupled to an associated electrode by a wire extending between the contact and the electrode, wherein the insulation layer positioned between the conductive layer and the conductive adhesive layer covers the wires and screens the wires from the conductive adhesive layer; and
   a pulse generator communicatively coupled to the electrode pad, the pulse generator operable to generate burst waveforms for delivery to the skin of the patient via the electrode pad.

2. The exogenous neurostimulation system of claim 1, wherein the electrode pad is in wired communication with the pulse generator.

3. The exogenous neurostimulation system of claim 1, wherein the electrode pad is in wireless communication with the pulse generator.

4. The exogenous neurostimulation system of claim 1, wherein the electrode pad comprises a non-conductive adhesive layer adjacent the substrate layer, wherein the substrate layer is positioned between the non-conductive adhesive layer and the conductive layer, and wherein the pulse generator is directly mechanically coupled to the electrode pad via the non-conductive adhesive layer.

5. The exogenous neurostimulation system of claim 1, wherein the pulse generator includes a clip configured to attach the pulse generator to a garment of the patient.

6. The exogenous neurostimulation system of claim 1, wherein the electrode pad is communicatively coupled to the pulse generator via a cable.

7. The exogenous neurostimulation system of claim 6, wherein the electrode pad comprises a plurality of ribbon contacts corresponding to the plurality of electrodes, the plurality of ribbon contacts engaging corresponding terminals of a connector included on the cable.

8. The exogenous neurostimulation system of claim 1, wherein the electrode pad is disposable after one or more uses and the pulse generator is reusable.

9. The exogenous neurostimulation system of claim 1, wherein the exogenous neurostimulation system is configured to electrically stimulate peripheral nerve targets.

10. A method of assembling an exogenous neurostimulation system, the method comprising:
    providing an electrode pad including a plurality of electrodes configured to be applied to skin of a patient, the electrode pad further including:
       a conductive adhesive layer configured to adhere to the skin of the patient;
       an insulation layer adjacent the conductive adhesive layer;
       a conductive layer adjacent the insulation layer and defining the plurality of electrodes, the insulation layer positioned between the conductive layer and the conductive adhesive layer;
       a substrate layer adjacent the conductive layer and supporting the conductive layer, the conductive layer positioned between the substrate layer and the insulation layer; and
       a plurality of contacts corresponding to the plurality of electrodes, each contact electrically coupled to an associated electrode by a wire extending between the contact and the electrode, wherein the insulation layer positioned between the conductive layer and the conductive adhesive layer covers the wires and screens the wires from the conductive adhesive layer; and
    communicatively coupling a pulse generator to the electrode pad, the pulse generator operable to generate burst waveforms for delivery to the skin of the patient via the electrode pad.

11. The method of claim 10, wherein communicatively coupling the pulse generator to the electrode pad comprises establishing a wired connection between the pulse generator and the electrode pad.

12. The method of claim 10, wherein communicatively coupling the pulse generator to the electrode pad comprises establishing a wireless connection between the pulse generator and the electrode pad.

13. The method of claim 10, wherein the electrode pad includes a non-conductive adhesive layer adjacent the substrate layer, wherein the substrate layer is positioned between the non-conductive adhesive layer and the conductive layer, and wherein the method further comprises directly mechanically coupling the pulse generator to the electrode pad via the non-conductive adhesive layer.

14. The method of claim 10, wherein the pulse generator includes a clip configured to attach the pulse generator to a garment of the patient.

15. The method of claim 10, wherein communicatively coupling the pulse generator to the electrode pad comprises communicatively coupling the pulse generator to the electrode pad using a cable.

16. The method of claim 15, wherein the electrode pad includes a plurality of ribbon contacts corresponding to the plurality of electrodes, the plurality of ribbon contacts engaging corresponding terminals of a connector included on the cable.

17. The method of claim 10, wherein the electrode pad is disposable one or more uses and the pulse generator is reusable.

18. The method of claim 10, wherein the plurality of electrodes includes at least four electrodes arranged in a grid pattern.

\* \* \* \* \*